United States Patent [19]

Groh

[11] Patent Number: 5,527,488

[45] Date of Patent: Jun. 18, 1996

[54] HIGH VISCOSITY ANHYDROUS MAKEUP REMOVER GEL

[75] Inventor: David G. Groh, Grand Rapids, Mich.

[73] Assignee: Amway Corporation, Ada, Mich.

[21] Appl. No.: 402,760

[22] Filed: Mar. 10, 1995

Related U.S. Application Data

[63] Continuation of Ser. No. 926,962, Aug. 7, 1992, abandoned.

[51] Int. Cl.[6] .................................................. C09D 9/00
[52] U.S. Cl. .................. 252/170; 252/174.23; 252/89.1; 252/DIG. 5
[58] Field of Search .................. 252/174.21, 174.23, 252/DIG. 5, 170, 89.1

[56] References Cited

U.S. PATENT DOCUMENTS

| | | | |
|---|---|---|---|
| 923,850 | 6/1909 | Kayser | 252/135 |
| 1,419,625 | 6/1922 | Guernsey | 252/135 |
| 3,277,013 | 10/1966 | Gianladis | 252/153 |
| 3,383,320 | 5/1968 | Bell, Jr. | 252/132 |
| 3,567,784 | 3/1971 | Tsatsos et al. | 568/625 |
| 3,645,904 | 2/1972 | Beach | 252/174.23 |
| 3,682,849 | 8/1972 | Smith et al. | 568/622 |
| 3,790,488 | 2/1974 | Iino | 252/174.23 |
| 3,795,624 | 3/1974 | Feinstone | 252/91 |
| 3,943,178 | 3/1976 | Stein et al. | 568/622 |
| 3,956,401 | 5/1976 | Scardera et al. | 568/625 |
| 3,962,150 | 6/1976 | Viola | 252/542 |
| 4,140,656 | 2/1979 | Mast | 252/545 |
| 4,322,545 | 3/1982 | Scala, Jr. | 560/103 |
| 4,474,678 | 10/1984 | Lutz et al. | 252/174.21 |
| 4,543,205 | 9/1985 | Contamin | 252/546 |
| 4,664,835 | 5/1987 | Grollier et al. | 252/90 |
| 4,673,526 | 6/1987 | Zabotto et al. | 252/174.16 |
| 4,935,228 | 6/1990 | Finkenaur et al. | 424/64 |
| 4,968,447 | 11/1990 | Dixon et al. | 252/174.23 |
| 5,160,739 | 11/1992 | Kanga | 424/401 |

FOREIGN PATENT DOCUMENTS

| | | |
|---|---|---|
| 339355 | 12/1930 | United Kingdom . |
| 522097 | 6/1940 | United Kingdom . |

*Primary Examiner*—Peter D. Mulcahy
*Attorney, Agent, or Firm*—Amway Corporation

[57] ABSTRACT

A high viscosity gel-type anhydrous makeup remover composition is disclosed. The composition comprises polyethylene, polyethylene copolymer and a gelable oil base, which base can be comprised of a mixture of mineral oils and branched natural or branched synthetic esters, or a mixture of just branched natural or branched synthetic esters. In some embodiments the composition further includes branched non-ionic alkoxylated alcohol surfactants with at least a 20 carbon branched chain, a preservative mixture and a mixture of natural oils.

6 Claims, No Drawings

HIGH VISCOSITY ANHYDROUS MAKEUP REMOVER GEL

This is a continuation of application Ser. No. 07/926,962 filed on Aug. 7, 1992 now abandoned.

BACKGROUND OF THE INVENTION

The present invention relates to the field of makeup remover compositions, i.e., compositions which, when applied to the skin, remove makeup and dirt from the skin. More particularly, the invention relates to the field of anhydrous makeup remover compositions which are in the form of a high viscosity gel.

There are many different types of makeup compositions in the prior art. Generally, these compositions are classified into two categories: anhydrous or oil-based and water-based. The conventional anhydrous or oil-based makeup remover system has two advantages over the water-based system. First, the anhydrous or oil-based system is usable and effective on all makeup products on the market, both water rinsable and waterproof. The second advantage of the anhydrous or oil-based makeup remover system is that such a system does not necessarily require the addition of preservatives to prevent microorganism growth.

Various problems have been encountered in the prior art in formulating an anhydrous or oil-based makeup remover composition. These problems include producing a makeup remover composition which, when removed from the skin, does not leave behind a greasy or oily film or feel. Another problem encountered in prior art compositions is formulating an anhydrous or oil base gelled system which produces a composition with a low liquid syneresis tendency, as well as a high viscosity. The ability to provide a composition which has a low liquid syneresis is particularly important when the product is being applied by the user to a very small surface area such as the eyelid. Additionally, another disadvantage of the compositions found in the prior art is that such compositions have a tendency to be unstable in areas of high temperature. A further disadvantage found in compositions of the prior art is that many compositions, when applied to sensitive areas of the face such as the eyelid, create irritability to the skin.

Relevant related art discloses an anhydrous skin cleansing composition containing an oil phase, an emulsifying agent, and particulate water soluble polymeric abrasive particles resulting in a composition with a viscosity of 1–200 poise. The composition comprises (a) 50–90% of an oily phase; (b) 1–30% of an emulsifying agent; and (c) 1–10% of a polymeric particulate abrasive.

Other relevant art includes makeup removal through the use of a woven pad which is impregnated with an anhydrous composition. The anhydrous composition comprises a non-ionic surfactant selected from either esters of a polyethylene glycol or esters of sorbitol with fatty acids, and polyethenoxy esters of alkanes having 12–18 carbon atoms and at least one dermatologically acceptable vehicle selected from the group consisting of a mineral oil; a lower alkyl ester of fatty acid having 12–18 carbon atoms and an alkanol having 8–18 carbon atoms.

Another relevant composition found in the art discloses an anhydrous clear gel facial cleaner wherein mineral oil is the principal active ingredient. This composition teaches an anhydrous makeup remover comprising (a) mineral oil; (b) a straight chain carbon ester; and (c) a high molecular weight carboxy vinyl polymer comprised of acrylic acid which is cross-linked with a polymer of a copolymerized polyalkanol polyether.

SUMMARY OF THE INVENTION

Briefly stated, these and other problems in the prior art are solved by providing an anhydrous makeup remover composition with a high viscosity and low levels of liquid syneresis. The composition of the present invention includes between about 60 and 85% by weight of a gelable oil base, between 5 and 25% by weight of polyethylene and between 5 and 15% by weight of a polyethylene copolymer wherein the composition has a viscosity ranging from 7,000 to 15,000 poise. A preferred embodiment further includes between 0.1 and 20% by weight of a 100% active non-ionic surfactant preferably with at least a 20 carbon branched chain. The composition of the present invention can also include between 0.01–5% by weight of a preservative as well as anti-irritant and natural oils between 0.15 and 1.00%.

The oil base of the present invention can be comprised of mineral oils or natural or synthetic branched esters or a mixture of mineral oils and such esters. The addition of the branched ester or mixture of esters has the advantage over the related art of providing for a composition which has a generally non-greasy feel to it. Further, the addition of branched esters provide for enhanced protection against liquid syneresis of the gel matrix.

The polyethylene copolymer and polyethylene provide additional advantages over the related art in that the addition of these further enhances the prevention of liquid syneresis. This has the advantage of providing for a product with long-term stability which will not melt prior to being placed on the skin.

The addition of a 100% active non-ionic surfactant with at least a 20 carbon branched chain provides the further advantage of assisting in the prevention of syneresis of the final gel product. Preferably, the surfactant is a non-ionic alkoxylated alcohol surfactant which aids in a low irritability level of the composition when applied to sensitive areas such as the eyelid.

The composition of the present invention can also include between 0.01 and 5% of a preservative mixture, which mixture preferably would include glyceryl laurate in an amount ranging from 0.01 and 2%, methyl paraben in an amount ranging from 0.01 and 2%, and phenoxyethanol in an amount ranging from 0.01 and 3%.

Anti-irritant oils such as alpha bisabolol and other natural oils such as apricot kernel oil and avocado oil can also be added in a range from 0.15 and 1.00%.

The high viscosity gel composition of the present invention has the advantage over the related art of providing for a product which is easier to handle by the consumer and can be applied accurately to small surface areas such as the eyelid. Further, the product has the advantage of being non-irritating to sensitive areas of the skin. Additionally, the product, once in contact with the skin, will break down its gel structure upon application of pressure, rather than the gel matrix breaking down prior to application. Thereafter, the composition, as well as the makeup being removed, can be wiped off of the skin leaving a generally non-greasy feel.

It is noted that unless otherwise indicated, the percentages as stated in the specification and the appended claims are intended to refer to percentages by weight of the total composition.

The present invention, together with attendant objects and advantages, will be best understood with reference to the detailed description below.

DETAILED DESCRIPTION OF THE PREFERRED EMBODIMENTS

As mentioned above, the makeup remover composition of the present invention is an anhydrous high viscosity gel-type product comprising an oil base capable of gelling, a polyethylene copolymer, a polyethylene and, in some instances, a branched active surfactant, a preservative mixture and a mixture of natural oils.

In accordance with a preferred embodiment of the invention, the oil base of the present invention, which is capable of gelling upon the addition of additional reagents, ranges from 60–85% of the composition. The oil base can be comprised of mineral oils or a natural or synthetic branched ester or a mixture of mineral oils and such esters. More preferably, the oil base comprises synthetic or natural esters or a mixture of such esters with branched structures. In one preferred embodiment the oil base is comprised of a mixture of glyceryl trioctanoate in an amount between 45 and 80%, cetyl octanoate in an amount between 0.50 and 10% and caprylic capric triglycerides in an amount ranging from between 0.50 and 15%. The oil base of the most preferred embodiment of the present invention comprises a mixture of mineral oils in an amount of 58.75% and octyl isononoate in an amount of 20%. Other natural and synthetic esters than those cited above can be used in the composition such as glyceryl caprylate caprate, among others.

In a preferred embodiment the composition further includes between 5 and 25% by weight of polyethylene, most preferably 12% by weight, and between 5 and 15% by weight of polyethylene copolymer, most preferably 8% by weight. The polyethylene copolymer can be ethylene-polyvinyl acetate copolymer or ethylene vinyl acetate copolymer, with ethylene vinyl acetate copolymer preferred. The addition of polyethylene and ethylene vinyl acetate copolymer has advantages over the related art as the polyethylene and polyethylene copolymer further adds to the prevention of liquid syneresis. Preferably, the polyethylene used in the composition will have a molecular weight of between about 1,100 and 5,000 and a hardness of 7.0 (dmm), a drop point temperature of 102° C. and a density of 0.91. In the most preferred embodiment the polyethylene is one such as that obtained from Allied Signal under the designation AC617A. The polyethylene copolymer will preferably have a molecular weight of between 2,000 and 8,000, a drop point temperature of 95° C., hardness of 9.5 (dmm) and a density of 0.92. In the most preferred embodiment the polyethylene copolymer will consist of ethylene vinyl acetate and is one such as that obtained from Allied Signal under the designation AC400.

The polyethylene and polyethylene copolymer is important to the present composition because they act as the gelling agent for the composition. More importantly, the polyethylene and polyethylene copolymer aid in the high viscosity achieved in the final product, which viscosity is in the range of 7,000 to 15,000 and acts to decrease the leakage of liquid from the gel matrix as well as providing a product which is easy to use by the consumer on small surface areas.

In a preferred embodiment the composition additionally includes between 0.1 and 20% by weight of a 100% active non-ionic surfactant with at least a 20 carbon branched chain, preferably an alkoxylated alcohol surfactant. In the most preferred embodiment the surfactant is octyldodeceth-25, although others such as methyl glucose sesquiio stearate, PEG-60 sorbitan tetrastearate and PEG-60 hydrogenated castor oil can be used.

A preferred embodiment of the present invention can also include between 0.01 and 5% by weight of a preservative, although a preservative in an anhydrous closed system is not necessary. The compositions of the aforementioned preferred embodiments can comprise a preservative mixture of glyceryl laurate in an amount ranging from 0.01 and 2% by weight, preferably 0.10% by weight, methyl paraben in an amount ranging from 0.01 and 2% by weight, preferably 0.10% by weight, and phenoxyethanol in an amount ranging from 0.01 and 3% by weight, preferably in an amount of 0.30% by weight. Because the preferred composition is anhydrous, the risk of microorganism growth within the composition is small and, therefore, the most preferred embodiment contains only minute amounts of the preservative mixture. The preservative is used only in the event that water has accidentally entered into the composition during the manufacturing process.

In a preferred embodiment anti-irritant oils such as alpha bisabolol in an amount of 0.05% and other natural oils such as apricot kernel oil in an amount of 0.35% and avocado oil in an amount of 0.35% are additionally added.

In one preferred embodiment of the present invention the composition comprises glyceryl trioctanoate in an amount of 56%, cetyl octanoate in an amount of 5%, caprylic capric triglycerides in an amount of 2.5%, 12% of polyethylene (AC617), 8% of ethylene vinyl acetate (AC400), 16% of a non-ionic alkoxylated alcohol surfactant having at least a 20 carbon branched chain, most preferably octyldodeceth-25, and a preservative mixture of 0.10% glyceryl laurate, 0.10% methyl paraben and 0.30% phenoxyethanol.

In the most preferred embodiment of the present invention the composition comprises mineral oil in an amount of 58.75%, octyl isononoate in an amount of 20%, polyethylene in an amount of 12%, ethylene vinyl acetate in an amount of 8%, glyceryl laurate in an amount of 0.10%, methyl paraben in an amount of 0.10%, phenoxyethanol in an amount of 0.30%, alpha bisabolol in an amount of 0.05%, apricot kernel oil in an amount of 0.35% and avocado oil in an amount of 0.35%.

To provide a better understanding of the invention, several examples of the anhydrous makeup remover composition of the present invention are given as an illustration and with no limitative nature whatsoever. Example I represents the most preferred embodiment of the present composition.

| CHEMICAL NAME | % (WT/WT) | | | | | | | | |
| --- | --- | --- | --- | --- | --- | --- | --- | --- | --- |
| | EX I | EX II | EX III | EX IV | EX V | EX VI | EX VII | EX VIII | EX IX |
| Polyethylene | 12.00 | 12.00 | 12.00 | 12.00 | 12.00 | 12.00 | 10.00 | 20.00 | 10.00 |
| Ethylene Vinyl Acetate (AC400) | 8.00 | 8.00 | 8.00 | 8.00 | 8.00 | 8.00 | 5.00 | 5.00 | 15.00 |
| Ethylene Polyvinyl Acetate | | | | | | | | | |
| Mineral Oil | 58.75 | | | | | | 10.00 | 65.00 | |
| Caprylic Capric Triglycerides | | 2.50 | 57.50 | | 59.50 | 79.50 | | | 60.00 |

|  | % (WT/WT) | | | | | | | | |
|---|---|---|---|---|---|---|---|---|---|
| Glyceryl Trioctanoate |  | 56.00 |  | 59.50 |  |  | 50.00 |  | 10.00 |
| Octyl Isononanoate | 20.00 |  | 20.00 | 20.00 | 6.00 |  | 18.00 | 10.00 |  |
| Triisocetyl Citrate |  |  |  |  | 14.00 |  |  |  | 5.00 |
| Cetyl Octanoate |  | 5.00 |  |  |  |  |  |  |  |
| Octyldodeceth-25 |  | 16.00 |  |  |  |  |  |  |  |
| Methyl Glucose Sesquiisostearate |  |  |  |  |  |  |  |  |  |
| PEG-60 Sorbitan Tetrastearate |  |  |  |  |  |  |  |  |  |
| PEG-60 Hydrogenated Castor Oil |  |  |  |  |  |  |  |  |  |
| Glyceryl Caprylate Caprate |  |  |  | 2.00 |  |  |  |  |  |
| Methyl Paraben | 0.10 | 0.10 | 0.10 | 0.10 | 0.10 | 0.10 | 2.00 |  |  |
| Glyceryl Laurate | 0.10 | 0.10 | 0.10 | 0.10 | 0.10 | 0.10 | 2.00 |  |  |
| Phenoxyethanol | 0.30 | 0.30 | 0.30 | 0.30 | 0.30 | 0.30 | 3.00 |  |  |
| Alpha Bisabolol | 0.05 |  |  |  |  |  |  |  |  |
| Apricot Kernel Oil | 0.35 |  |  |  |  |  |  |  |  |
| Avocado Oil | 0.35 |  |  |  |  |  |  |  |  |
| TOTAL | 100.00 | 100.00 | 100.00 | 100.00 | 100.00 | 100.00 | 100.00 | 100.00 | 100.00 |

| CHEMICAL NAME | EX X | EX XI | EX XII | EX XIII | EX XIV | EX XV | EX XVI | EX XVII | EX XVIII |
|---|---|---|---|---|---|---|---|---|---|
| Polyethylene | 12.00 | 10.00 | 15.00 | 10.00 | 12.00 | 14.00 | 12.00 | 12.00 | 12.00 |
| Ethylene Vinyl Acetate (AC400) | 8.00 | 5.00 |  |  | 8.00 | 10.00 | 8.00 | 8.00 | 8.00 |
| Ethylene Polyvinyl Acetate |  |  | 5.00 | 15.00 |  |  |  |  |  |
| Mineral Oil |  | 60.00 | 50.00 |  | 50.00 | 55.00 |  |  |  |
| Caprylic Capric Triglycerides |  |  |  | 50.00 |  |  | 4.00 | 5.00 | 55.00 |
| Glyceryl Trioctanoate | 20.00 | 4.00 |  |  |  |  | 45.00 | 40.00 | 20.00 |
| Octyl Isononanoate | 59.00 | 20.00 |  | 10.00 | 5.00 | 20.00 | 20.00 | 15.00 |  |
| Triisocetyl Citrate |  |  | 20.00 |  |  |  |  |  |  |
| Cetyl Octanoate |  |  |  |  |  | 10.00 |  |  |  |
| Octyldodeceth-25 |  | 0.10 |  |  |  |  |  | 20.00 |  |
| Methyl Glucose Sesquiisostearate |  |  | 10.00 |  |  | 0.90 |  |  | 4.00 |
| PEG-60 Sorbitan Tetrastearate |  |  |  | 4.00 |  |  | 0.50 |  |  |
| PEG-60 Hydrogenated Castor Oil |  |  |  | 10.00 |  |  | 0.50 |  |  |
| Glyceryl Caprylate Caprate |  |  |  |  |  | 10.00 |  |  |  |
| Methyl Paraben | 0.10 |  |  | 0.25 |  | 0.10 |  |  | 0.01 |
| Glyceryl Laurate |  |  |  | 0.25 |  |  |  |  | 0.01 |
| Phenoxyethanol | 0.90 | 0.90 |  | 0.50 |  |  |  |  | 0.01 |
| Alpha Bisabolol |  |  |  |  | 5.00 |  |  |  | 0.07 |
| Apricot Kernel Oil |  |  |  |  | 5.00 |  |  |  | 0.45 |
| Avocado Oil |  |  |  |  | 5.00 |  |  |  | 0.45 |
| TOTAL | 100.00 | 100.00 | 100.00 | 100.00 | 100.00 | 100.00 | 100.00 | 100.00 | 100.00 |

The embodiments of the invention in which an exclusive property or privilege is claimed are defined as follows.

1. A high viscosity anhydrous eye makeup remover composition for application to the skin on and around the eyelid consisting essentially of: from about 60–85% by weight of a non-irritating oil base capable of gelling wherein said base consists essentially of glyceryl trioctanoate in an amount ranging from 45–80% by weight of said oil base, cetyl octanoate in an amount ranging from 0.50–10% by weight of said oil base, and caprylic capric triglycerides in an amount ranging from 0.50–15% by weight of said oil base, from 10–25% by weight of polyethylene and from 5–15% by weight of ethylene vinyl acetate copolymer wherein the weight proportion of the polyethylene to the ethylene vinyl acetate copolymer is in the range of about 0.67:1 to about 2.0:1. respectively, when the polyethylene is present in major proportion and wherein the weight proportion of the polyethylene to the ethylene vinyl acetate copolymer is greater than about 0.67:1 when the ethylene vinyl acetate is present in major proportion, the composition having a viscosity in the range of 7,000 to 15,000 poise.

2. A non-irritating high viscosity anhydrous eye makeup remover composition consisting essentially of 58.75% mineral oil, 12% polyethylene, 8% ethylene vinyl acetate copolymer, 20% octyl isononanoate, 0.10% glyceryl laurate, 0.10% methyl paraben, 0.30% phenoxyethanol, 0.05 alpha bisabolol, 0.35% apricot kernel oil and 0.35% avocado oil the composition having a viscosity in the range of 7,000 to 15,000 poise.

3. The high viscosity anhydrous eye makeup remover composition of claim 1 wherein said polyethylene comprises 12% by weight of the total composition and said ethylene vinyl acetate copolymer comprises 8% by weight of the total composition.

4. The high viscosity eye makeup remover of claim 1 further comprising from 0.1–20% by weight of a 100% active non-ionic alkoxylated alcohol surfactant having at least a 20 carbon branched chain.

5. A high viscosity anhydrous non-irritating eye make-up remover composition for application to the skin on and around the eyelid consisting essentially of:

a) from between about 60 to 85% of an oil base capable of gelling wherein said base consists essentially of:
  i) glyceryl trioctanoate in an amount ranging from 45–80% by weight of said oil base;
  ii) cetyl octanoate in an amount ranging from 0.50–10% by weight of said oil base; and
  iii) caprylic capric triglycerides in an amount ranging from 0.50–15% by weight of said oil base;

b) from 10% to 25% by weight of polyethylene;

c) from 5% to 15% by weight of ethylene vinyl acetate wherein the weight proportion of the polyethylene to the ethylene vinyl acetate copolymer is in the range of about 0.67:1 to about 2.0:1, respectively, when the polyethylene is present in major proportion and wherein the weight proportion of the polyethylene to the ethylene vinyl acetate copolymer is greater than about 0.67:1 when the ethylene vinyl acetate is present in major proportion;

d) from 0.1 to 20% by weight of a 100 percent active non-ionic alkoxylated alcohol surfactant having at least a 20 carbon branched chain;

e) from 0.1 to 5% by weight of a preservative; and f) from 0% to 1.00% by weight of a natural oil, the composition having a viscosity in the range of 7,000 to 15,000 poise.

6. A high viscosity anhydrous non-irritating eye make-up remover composition for application to the skin on and around the eyelid consisting essentially of:

a) from 10 to 65% by weight mineral oil;

b) from 5 to 20% by weight octyl isononanoate;

c) from 0% to 50% by weight of a branched ester selected from the group consisting of glyceryl trioctanoate and cetyl octanoate;

d) from 10% to 20% of polyethylene;

e) from 5% to 10% by weight of ethylene vinyl acetate wherein the weight proportion of the polyethylene to the ethylene vinyl acetate copolymer is in the range of about 1:1 to about 2.0:1, respectively, when the polyethylene is present in major proportion and wherein the weight proportion of the polyethylene to the ethylene vinyl acetate copolymer is greater than about 0.67:1 when the ethylene vinyl acetate is present in major proportion;

f) from 0% to 10% by weight of a 100 percent active non-ionic alkoxylated alcohol surfactant having at least a 20 carbon branched chain;

g) from 0% to 7% by weight of a preservative or mixture of preservatives; and h) from 0% to 15% of a non-irritating oil or mixture of oils, the composition having a viscosity in the range of 7,000 to 15,000 poise.

* * * * *